United States Patent
Manca et al.

(10) Patent No.: US 12,120,779 B2
(45) Date of Patent: Oct. 15, 2024

(54) AEROSOL-GENERATING SYSTEM WITH PUMP

(71) Applicant: Altria Client Services LLC, Richmond, VA (US)

(72) Inventors: Laurent Manca, Sullens (CH); Rui Nuno Batista, Morges (CH)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 18/189,774

(22) Filed: Mar. 24, 2023

(65) Prior Publication Data

US 2023/0232498 A1 Jul. 20, 2023

Related U.S. Application Data

(63) Continuation of application No. 17/130,056, filed on Dec. 22, 2020, now Pat. No. 11,617,230, which is a (Continued)

(30) Foreign Application Priority Data

Mar. 31, 2016 (EP) ..................... 16163420

(51) Int. Cl.
*H05B 1/02* (2006.01)
*A24F 40/10* (2020.01)
(Continued)

(52) U.S. Cl.
CPC ........... *H05B 1/0244* (2013.01); *A24F 40/48* (2020.01); *A24F 40/485* (2020.01); *H05B 3/04* (2013.01);
(Continued)

(58) Field of Classification Search
CPC ... H05B 3/04; H05B 3/16; H05B 3/18; H05B 3/34; H05B 3/44; H05B 2203/01;
(Continued)

(56) References Cited

U.S. PATENT DOCUMENTS 5,666,977 A 9/1997 Higgins et al.
6,103,810 A 8/2000 Frayer et al.
(Continued)

FOREIGN PATENT DOCUMENTS

CN 1960777 A 5/2007
CN 103118728 A 5/2013
(Continued)

OTHER PUBLICATIONS

Extended European Search Report #16163420.9 dated Sep. 20, 2016.
(Continued)

*Primary Examiner* — Brian W Jennison
(74) *Attorney, Agent, or Firm* — Harness, Dickey & Pierce, P.L.C.

(57) ABSTRACT

An aerosol generating system includes a heater assembly and a manually operated pump. The pump includes a hollow member with an inlet portion and an outlet portion. The inlet portion of the hollow member is configured connectable with a liquid storage portion. The outlet portion of the hollow member is in fluid communication with a dispensing assembly. The pump is configured to dispense a liquid material onto the heater assembly. The pump is configured to pump the liquid material from the liquid storage portion via the dispensing assembly and onto the heater assembly.

18 Claims, 4 Drawing Sheets

Related U.S. Application Data continuation of application No. 15/474,337, filed on Mar. 30, 2017, now Pat. No. 10,905,163, which is a continuation of application No. PCT/EP2017/054253, filed on Feb. 23, 2017.

(51) Int. Cl.
*A24F 40/48* (2020.01)
*A24F 40/485* (2020.01)
*H05B 3/04* (2006.01)
*H05B 3/44* (2006.01)

(52) U.S. Cl.
CPC ............... *H05B 3/44* (2013.01); *A24F 40/10* (2020.01); *H05B 2203/014* (2013.01); *H05B 2203/021* (2013.01); *H05B 2203/022* (2013.01)

(58) Field of Classification Search
CPC ...... H05B 2203/02; A24F 47/00; A24F 40/48; A24F 40/10; A24F 40/485; A61M 11/042; A61M 11/006; A61M 15/06
See application file for complete search history.

(56) References Cited

U.S. PATENT DOCUMENTS

| | | | |
|---|---|---|---|
| 2002/0079309 A1 | 6/2002 | Cox et al. | |
| 2006/0196518 A1 | 9/2006 | Hon | |
| 2009/0223513 A1* | 9/2009 | Papania | B05B 17/0638 128/200.14 |
| 2010/0242975 A1 | 9/2010 | Hearn | |
| 2010/0242976 A1 | 9/2010 | Katayama et al. | |
| 2013/0213418 A1 | 8/2013 | Tucker et al. | |
| 2013/0263869 A1 | 10/2013 | Zhu | |
| 2014/0261487 A1 | 9/2014 | Chapman et al. | |
| 2014/0261492 A1* | 9/2014 | Kane | A24F 40/485 131/328 |
| 2015/0027456 A1 | 1/2015 | Janardhan et al. | |
| 2015/0027468 A1* | 1/2015 | Li | A24D 3/063 131/329 |
| 2015/0276262 A1 | 10/2015 | Dai et al. | |

FOREIGN PATENT DOCUMENTS

| | | |
|---|---|---|
| CN | 105142443 A | 12/2015 |
| CN | 105307520 A | 2/2016 |
| CN | 205108619 U | 3/2016 |
| EP | 0845220 A1 | 6/1998 |
| EP | 0957959 B1 | 9/2007 |
| EP | 2218760 A1 | 8/2010 |
| WO | WO-2016/005530 A1 | 1/2016 |
| WO | WO-2016/005531 A1 | 1/2016 |
| WO | WO-2016/005533 A1 | 1/2016 |
| WO | WO-2016/005600 A1 | 1/2016 |
| WO | WO-2016/005601 A1 | 1/2016 |
| WO | WO-2016/005602 A1 | 1/2016 |

OTHER PUBLICATIONS

International Search Report and Written Opinion issued May 19, 2017 in International Application No. PCT/EP2017/054253.
Spraying Systems Co., Experts in Spray Techonology, Dec. 13, 2018, www.spray.com.
Lee Products LTD, Innovation in Minaure, Dec. 13, 2018, www.leeproducts.co.uk.
Morphy Richards Redefine, Redefine your Expectations, Dec. 13, 2018, http://www.morphyrichardsredefine.com/.
Lee Products LTD, Check Valves, Dec. 13, 2018, http://www.industrial-microhydraulics.co.uk/check_valves.htm.
International Preliminary Report on Patentability and Written Opinion for corresponding International Application No. PCT/EP2017/054253 dated Oct. 2, 2018.
Russian Office Action and Search Report for corresponding Application No. 2018138160, dated May 21, 2020.
Russian Decision to Grant for corresponding Application No. 2018138160, dated Aug. 28, 2020.
Chinese Office Action dated Sep. 27, 2020 for corresponding Chinese Application No. 201780018410.0, and English-language translation thereof.
Notice of Allowance dated Feb. 4, 2021 issued in corresponding Japanese Patent Application No. 2018-549552.
Office Action issued Jun. 15, 2021 in Chinese Application No. 201780018410.0.
European Notice of Allowance dated Nov. 8, 2021 for corresponding European Application No. 17707004.2.
Chinese Office Action dated Dec. 16, 2021 for corresponding Chinese Application No. 201780018410.0, and English-language translation thereof.
Office Action dated Nov. 15, 2023 issued in related Korean patent application No. 10-2018-7030021.
Notice of Allowance dated Jul. 5, 2024 issued in the Korean patent application No. 10-2018-7030021.
Office Action dated Jul. 23, 2024 issued in Chinese patent application No. 201780018410.0.

* cited by examiner

AEROSOL-GENERATING SYSTEM WITH PUMP

This application is a continuation of U.S. application Ser. No. 17/130,056, filed on Dec. 22, 2020, which is a continuation of U.S. application Ser. No. 15/474,337, filed on Mar. 30, 2017, which is a continuation of and claims priority to PCT/EP2017/054253 filed on Feb. 23, 2017, and further claims priority to EP 16163420.9 filed on Mar. 31, 2016; the contents of each of which are hereby incorporated by reference in their entirety.

BACKGROUND

At least one example embodiment relates to a delivery system for liquid aerosol-forming substrate for use in an aerosol-generating system, such as a handheld electrically operated aerosol-generating system. At least one example embodiment also relates to an aerosol-generating system comprising such delivery system and a method of generating an aerosol in an aerosol-generating system.

Handheld electrically operated aerosol-generating systems may consist of a device portion comprising a battery and control electronics, a cartridge portion comprising a supply of an aerosol-forming substrate held in a liquid storage portion, and an electrically operated vaporizer, and a mouthpiece. The vaporizer may comprise a coil of heater wire wound around an elongate wick soaked in the liquid aerosol-forming substrate held in the liquid storage portion.

EP 0 957 959 B1 generally discloses an electrically operated aerosol generator configured to receive liquid material from a source. The aerosol generator comprisies an electrical pump configured to pump the liquid material in metered amounts from the source through a tube with an open end. A heating element is provided which surrounds the tube. The liquid material within the tube is volatilized upon activation of the heater. Upon volatilization the liquid material expands and exits the open end of the tube in gaseous form.

It would be desirable to provide an aerosol-generating system with a low-maintenance liquid delivery system and with an atomization effect.

SUMMARY

At least one example embodiment relates to an aerosol generating system. The aerosol generating system comprises a heater assembly and a manually operated pump. The manually operated pump defines a pumping volume having an inlet portion and an outlet portion. The inlet portion of the manually operated pump is configured to be connectable to a liquid storage portion. The outlet portion of the manually operated pump is in fluid connection with a dispensing assembly. The dispensing assembly is configured to dispense the liquid aerosol-forming substrate onto the heater assembly. The manually operated pump is configured to pump the liquid aerosol-forming substrate from the liquid storage portion via the dispensing assembly onto the heater assembly.

In at least one example embodiment, the liquid aerosol-forming substrate can be dispensed onto the heater assembly without the need for any electrically driven pumping system. Thus, the number of electric or electronic components, which might be prone to electro-mechanical malfunction, is reduced. Further, the wiring scheme of such delivery systems is less complex, such that not only maintenance, but also assembly of the aerosol-generating system is simplified.

The pumping volume of the manually operated pump may be defined by a hollow member having at least one wall. At least a portion of the wall is flexible. In other example embodiments, the pumping volume of the manually operated pump may be defined by a hollow member having at least one wall and a plunger moveable within the hollow member. The term "pumping volume" as used herein is defined as the internal volume of the hollow member extending between the inlet and the outlet of the hollow member. In some example embodiments, the hollow member defining the pumping volume may be a hollow flexible member, such as a hollow flexible tube. Using a hollow flexible tube with its two ends forming the inlet and the outlet portion, results in a particularly simple and reliable design that may be produced in a cost-efficient manner.

The manually activated pump may comprise a volume modifier. The volume modifier is configured to change the pumping volume of the manually operated pump. The volume modifier may be configured to be operated manually. The volume modifier may comprise a moveable element that engages with the at least one flexible portion of the wall or plunger of the pumping volume. When the volume modifier is operated, the moveable element may be pressed against the at least one flexible portion or plunger of the hollow member such that the internal volume of the hollow member is changed. When the moveable element is pressed against the at least one flexible portion or plunger of the hollow member, the internal volume of the hollow member is reduced creating an overpressure in the pumping volume. Due to this overpressure excess liquid aerosol-forming substrate contained in the pumping volume is ejected through the outlet portion of the pump volume. When the moveable element is released from the at least one flexible portion or plunger of the hollow member, the internal volume of the hollow member expands to its original size, thereby creating an underpressure in the pumping volume. Due to this underpressure liquid aerosol-forming substrate is pumped from the liquid storage portion into the pumping volume of the hollow member.

The inlet portion and the outlet portion of the hollow member of the manually operated pump may each comprise a one-way valve. The one-way valve at the inlet portion of the hollow member may only allow liquid flow from a connected liquid storage portion into the pumping volume. The one-way valve at the outlet portion of the hollow member may only allow liquid flow from the pumping volume to the dispensing assembly.

Any commercially available one-way valve with adequate size and liquid flows may be used, including mini and micro flutter valves, duckbill valves, or check valves. The valves may be made for example of materials resistant to aggressive chemicals or materials which may be used for food industry and medical applications.

In at least one example embodiment, the pumping volume is defined by a hollow flexible tube having an outlet portion and an inlet portion, which are each provided with a one-way valve. The volume modifier comprises a movable element and a fixed element. The flexible tube is positioned between the fixed element and the movable element of the volume modifier, such that by moving the movable element towards the fixed element, the internal volume of the tube is reduced.

The moveable member of the volume modifier may be connected to a button provided in the housing of the aerosol-generating system, such that the volume modifier can be operated.

A resilient member may be provided, which ensures that the moveable member is returned to its original position, once the volume modifier is released.

The size of the hollow element and collapsible proportions of the hollow element during operation of the pumping unit are directly related to the volume of liquid dispensed onto the heater assembly for creation of the aerosol and may be limited to specify a maximum liquid volume per pumping pulse. In some example embodiments employing a flexible hollow tube, the external diameter of the tube may range from about 2 millimeters (mm) to about 8 mm, and may range from about 3 mm to about 5 mm.

The desired and/or maximum amount of liquid to be pumped as a dose for a puff may be a small volume ranging from about 0.010 microliters to about 0.060 microliters (e.g., about 0.0125 microliters).

The force and the displacement required to squeeze the hollow member of the manually operated pump are very small. The resilient member may therefore also be used in order to define a reduced and/or minimum required force for operating the volume modifier. This force can generally be freely chosen and may be adapted to preferences. The force may be adjusted to range from about 0.1 newton to 1.0 newton (e.g, about 0.5 newton to about 0.8 newton).

The displacements of the moveable member may also be freely chosen and may be adapted to the design of specific example embodiments. The displacement may be adjusted to vary from about 0.4 mm to about 5.0 mm and may vary from about 0.7 mm to about 3.0 mm.

The inlet portion of the manually operated pump is configured to connect to a liquid storage portion. The connection between the manually operated pump and the liquid storage portion may be a permanent connection or a releasable connection. In some example embodiments the liquid storage portion may be refillable. In some embodiments the liquid storage portion may be replaceable and may be exchanged when it is empty or when a different type of liquid for aerosol-generation is desired. The releasable connection between the manually operated pump and the liquid storage portion may be established by any suitable connection means, including a Luer taper connection (either the locking or fitting type).

The pump may be configured to pump liquid aerosol-forming substrates that are characterized by a relatively high viscosity as compared to water. The viscosity of a liquid aerosol-forming substrate may be in the range from about 10 millpascal second to about 500 millipascal seconds or in the range of about 17 millipascal seconds to about 86 millipascal seconds.

At the outlet end of the dispensing assembly a nozzle may be provided via which the liquid aerosol-forming substrate may be sprayed onto the heater assembly for volatilization and aerosol creation. The nozzle converts the flow of the liquid aerosol-forming substrate into a plurality of small droplets. The spray pattern of the droplets may be adapted to the shape of the heater assembly.

The delivery device may comprise a classic type atomizer spray nozzle, in which case a flow of air is supplied through the nozzle by the action of puffing, creating a pressurized air flow that will mix and act with the liquid creating an atomized spray in the outlet of the nozzle. Several commercially systems including nozzles that work with small volumes of liquid, in sizes that meet the requirements to fit in small portable devices are available. Another class of nozzle that may be used is an airless spray nozzle, sometimes referred to as a micro-spray nozzle. Such nozzles create micro spray cones in very small sizes. With this class of nozzles, the airflow management inside the device, namely inside the mouth piece, surrounds the nozzle and the heating element, flushing the heater assembly towards the outlet of the mouth piece, preferably including a turbulent air flow pattern of the aerosol exiting the mouth piece.

For either class of nozzle, the distance of the air gap between the delivery device and the sheet heater assembly facing the nozzle, is within a range of about 2 millimeters (mm) to about 10 mm or from about 3 mm to about 7 mm. Any type of spraying nozzles may be used. Airless nozzle 062 Minstac from manufacturer "The Lee Company" is an example of a suitable spray nozzle.

The heater assembly may comprise any type of heating element suitable for evaporating the liquid aerosol-forming substrate. The heater assembly may be substantially flat in some example embodiment, and may have any desired shape. The heater assembly for example may have a rectangular, polygonal, circular or oval shape and may have width and length dimensions ranging from about 3 mm to about 10 mm.

The heating element may comprise a thin, substantially flat, electrically conductive material, such as a mesh of fibers, a conductive film, or an array of heating strips, suitable for receiving and heating an aerosol-forming substrate in an aerosol generating system.

The heating element may comprise a plurality of openings. In at least one example embodiment, the heating element may comprise a mesh of fibers with interstices between the fibers. The heating element may comprise a thin film or plate, optionally perforated with small holes. The heating element may comprise an array of narrow heating strips connected in series.

The heater assembly may comprise a heat resistive substrate and a heating element provided in the heat resistive substrate or on a surface of the heat resistive substrate. The heat resistive substrate of the heater assembly may be made from glass, heat resistive glass, ceramics, silicon, semiconductors, metals or metal alloys.

The heat resistive substrate may be substantially flat and may have any shape. The heat resistive substrate may have a rectangular, polygonal, circular, or oval shape with, for example, width and length dimensions of about 3 mm to about 10 mm. The thickness of the heat resistive substrate may range from about 0.2 mm to about 2.5 mm. In some example embodiments the heat resistive substrate may be have a rectangular shape with a size of about 7×6 millimeters or 5×5 millimeters (L×W).

The heating element may be provided as a thin film coating provided to the surface of the heat resistive substrate. The heating element can be impregnated, deposited, or printed the surface of the heat resistive substrate. The material of the thin film heating element can be any suitable material which has convenient electrical properties and a sufficiently high adherence to the heat resistive substrate.

The heating element may be provided within the volume of the heat resistive substrate, may be sandwiched between two elements of the heat resistive substrate, or may be covered with a protective layer of heat resistive material.

In some example embodiments the liquid aerosol-forming substrate may be delivered to a front side of the heat resistive substrate and the heating element may be provided on a backside of the heat resistive substrate.

The heater assembly may be spaced apart from the dispensing assembly. By providing the heater assembly spaced apart from the delivery assembly, the amount of liquid aerosol-forming substrate delivered to the heater assembly can be better controlled compared to a vaporizer having a tubing segment for carrying flow of the liquid aerosol-forming substrate from the delivery assembly to the heater assembly. Undesired capillary actions due to such tubing segment can be reduced and/or avoided. When passing the air gap, the delivered amount of the liquid aerosol-forming substrate will be transformed into a jet of droplets before hitting the surface of the heater assembly. Thus, a uniform distribution of the delivered amount of the liquid aerosol-forming substrate on the heater assembly can be enhanced in some examples, leading to better controllability and repeatability of generating an aerosol with a desired (or, alternatively a predetermined) amount of vaporized aerosol-forming substrate per inhalation cycle.

The operating temperature of the heater assembly may range from about 120 degrees Celsius to about 210 degrees Celsius, or from about 150 degrees Celsius to about 180 degrees Celsius. In some example embodiments, the operating temperature can be varied.

The aerosol-generating system may be configured such that upon activation of the pumping unit, an electrical signal is generated and transmitted to the control unit. To this end the moveable member of the volume modifier may be connected to an electro-mechanical switch, which is in electrical communication with the control unit. Activation of the pumping unit may simultaneously also trigger the control unit to activate the heater assembly.

The electrical communication with the control unit can be established via corresponding wiring between the switch and the control unit. The electrical communication with the control unit may also be established via a wireless interface, such as the switch remotely sending signals to the control unit, which can be at the other end of the device relative to the position of the switch.

The switch may be designed as kinetic self-powered electronic component. Such kinetic electronic switches do not need wiring connection to the control unit and the power source, because the required electric energy for producing and sending the signals is generated by the action of pressing the switch button. Kinetic electronic switches for single button activation of remote signals are commercially available. Applicable solutions existing in the market include very compacted, small and thin electronics, including thin film flexible electronics. Eliminating or reducing wires and electrical contacts simplifies the design and assembly of the aerosol-generating system and improves overall reliability.

The kinetic electronic component may also communicate with further surrounding devices and in particular also with further electronic components, such as sensors, used in the aerosol-generating system.

The aerosol-generating system may be an electrically operated aerosol-generating system. The aerosol-generating system is portable. The aerosol-generating system may have a size comparable to a cigar or cigarette. The aerosol-generating system may have a total length ranging from about 30 mm to about 150 mm. The aerosol-generating system may have an external diameter ranging from about 5 mm to about 30 mm.

At least one example embodiment relates to a method for generating an aerosol. The method comprises providing a heater assembly, and providing a manually operated pump, comprising a hollow member with an inlet portion and an outlet portion. The inlet portion of the hollow member is configured to be connected to a liquid storage portion and the outlet portion of the hollow member is in fluid connection with a dispensing assembly. The method further includes operating the manually operated pump to pump a liquid aerosol-forming substrate from the liquid storage portion via the dispensing assembly onto a heater assembly.

Features described in relation to one example embodiment may equally be applied to other example embodiments.

BRIEF DESCRIPTION OF THE DRAWINGS

Embodiments will now be described, by way of example only, with reference to the accompanying drawings.

DETAILED DESCRIPTION

Various example embodiments will now be described more fully with reference to the accompanying drawings in which some example embodiments are shown. However, specific structural and functional details disclosed herein are merely representative for purposes of describing example embodiments. Thus, the embodiments may be embodied in many alternate forms and should not be construed as limited to only example embodiments set forth herein. Therefore, it should be understood that there is no intent to limit example embodiments to the particular forms disclosed, but on the contrary, example embodiments are to cover all modifications, equivalents, and alternatives falling within the scope.

In the drawings, the thicknesses of layers and regions may be exaggerated for clarity, and like numbers refer to like elements throughout the description of the figures.

Although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that, if an element is referred to as being "connected" or "coupled" to another element, it can be directly connected, or coupled, to the other element or intervening elements may be present. In contrast, if an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including,"

if used herein, specify the presence of stated features, integers, steps, operations, elements and/or components, but do not preclude the presence or addition of one or more other features, integers, steps, operations, elements, components and/or groups thereof.

Spatially relative terms (e.g., "beneath," "below," "lower," "above," "upper" and the like) may be used herein for ease of description to describe one element or a relationship between a feature and another element or feature as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, for example, the term "below" can encompass both an orientation that is above, as well as, below. The device may be otherwise oriented (rotated 90 degrees or viewed or referenced at other orientations) and the spatially relative descriptors used herein should be interpreted accordingly.

Example embodiments are described herein with reference to cross-sectional illustrations that are schematic illustrations of idealized embodiments (and intermediate structures). As such, variations from the shapes of the illustrations as a result, for example, of manufacturing techniques and/or tolerances, may be expected. Thus, example embodiments should not be construed as limited to the particular shapes of regions illustrated herein but may include deviations in shapes that result, for example, from manufacturing. For example, an implanted region illustrated as a rectangle may have rounded or curved features and/or a gradient (e.g., of implant concentration) at its edges rather than an abrupt change from an implanted region to a non-implanted region. Likewise, a buried region formed by implantation may result in some implantation in the region between the buried region and the surface through which the implantation may take place. Thus, the regions illustrated in the figures are schematic in nature and their shapes do not necessarily illustrate the actual shape of a region of a device and do not limit the scope.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Although corresponding plan views and/or perspective views of some cross-sectional view(s) may not be shown, the cross-sectional view(s) of device structures illustrated herein provide support for a plurality of device structures that extend along two different directions as would be illustrated in a plan view, and/or in three different directions as would be illustrated in a perspective view. The two different directions may or may not be orthogonal to each other. The three different directions may include a third direction that may be orthogonal to the two different directions. The plurality of device structures may be integrated in a same electronic device. For example, when a device structure (e.g., a memory cell structure or a transistor structure) is illustrated in a cross-sectional view, an electronic device may include a plurality of the device structures (e.g., memory cell structures or transistor structures), as would be illustrated by a plan view of the electronic device. The plurality of device structures may be arranged in an array and/or in a two-dimensional pattern.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

In order to more specifically describe example embodiments, various features will be described in detail with reference to the attached drawings. However, example embodiments described are not limited thereto.

Figure 1:
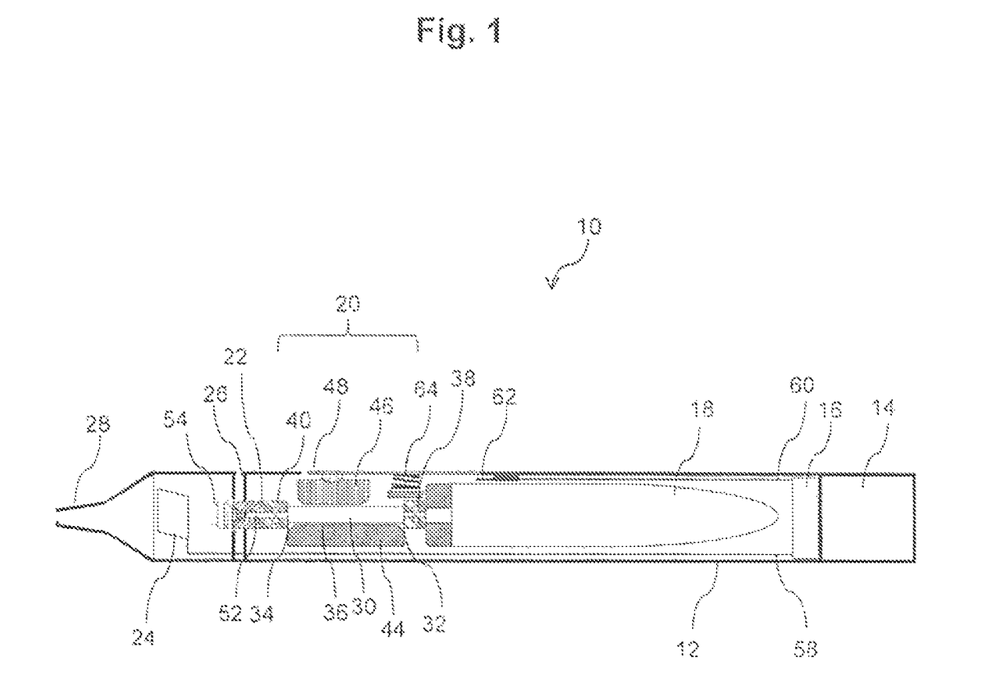
FIG. 1 is a cross-sectional view of an aerosol-generating system in standby mode according to at least one example embodiment.

In at least one example embodiment, as shown in FIG. 1, components of an aerosol-generating system are shown in an initial or stand-by mode. The aerosol-generating system 10 comprises a housing 12, a power source 14, a control unit 16, a liquid storage portion 18, a manually operated pump 20, a dispensing assembly 22 and a heater assembly 24. The housing 12 comprises an air inlet 26 and a mouthpiece 28 at a proximal end of the housing 12. During vaping, the mouthpiece is drawn upon so as to create an air stream from the air inlets 26, via the heater assembly 24 towards the mouthpiece 28.

In at least one example embodiment, the manually operated pump 20 is configured to collect liquid material from the liquid storage portion 18 and pump the liquid material in a controlled way onto the heater assembly 24. The pump 20 comprises a flexible hollow tube 30. The flexible hollow tube 30 includes an inlet portion 32 and an outlet portion 34. A a pumping volume 36 is between the inlet portion 32 and the outlet portion 34. At both ends of the tube 30, a one-way valve 38, 40 is provided. The one-way valve 38 at the inlet portion 32 is configured to allow entry of the liquid material into the pumping volume 36. The one-way valve 40 at the outlet portion 34 is configured to allow exit of the liquid material out of the pumping volume 36. A volume modifier comprises a fixed element 44 and a moveable element 46. The fixed element 44 and the moveable element 46 are provided at opposite sides of the flexible hollow tube 30. The moveable element 46 is connected to a button 48 provided in the housing 12 of the aerosol-generating system 10.

In at least one example embodiment, as shown in FIG. 1, the manually operated pump is depicted in the initial position in which the pumping volume is completely filled with liquid aerosol-forming substrate.

Figure 2:
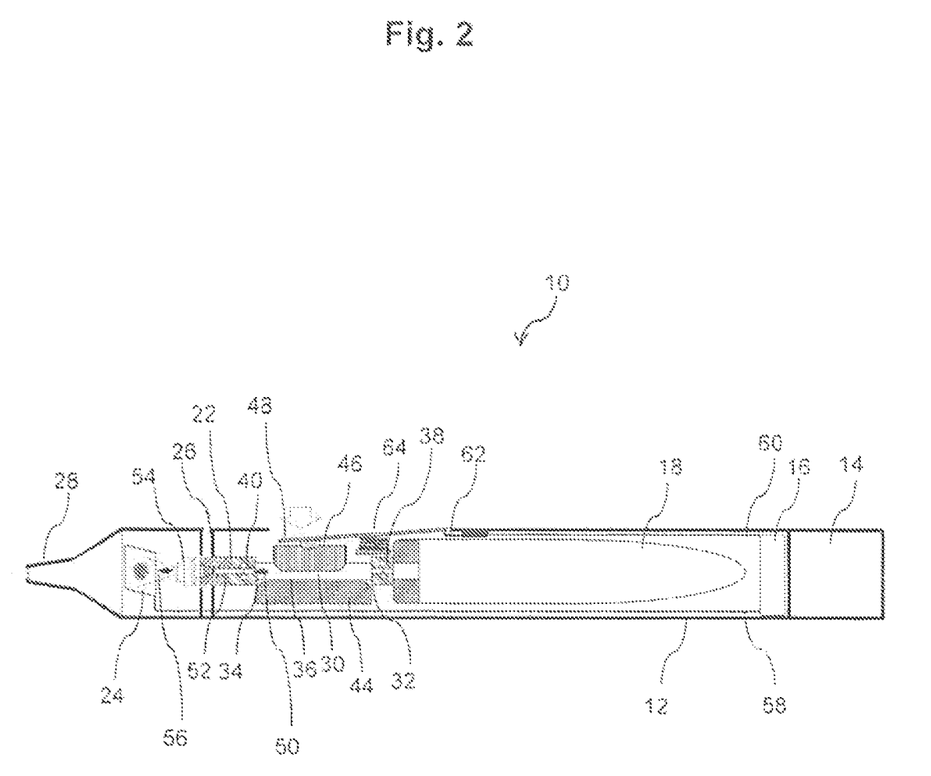
FIG. 2 is a cross-sectional view of the aersol-generating system of FIG. 1 showing the delivery system during manual operation of the volume modifier according to at least one example embodiment.

When the button 48 is pressed, as depicted in FIG. 2, the hollow tube 30 is squeezed between the moveable element 46 and the fixed element 44 so as to decrease the pumping volume 36. When the pumping volume 36 is decreased, an overpressure is created in the pumping volume 36. In order to compensate for the overpressure, a portion of the liquid material is ejected through the outlet portion 34 of hollow tube 30. This is indicated by arrow 50 in FIG. 2. Outlet portion 34 is in fluid communication with the dispensing assembly 22. The dispensing assembly 22 comprises a tubing 52 and a spray nozzle 54. The spray nozzle 54 is an airless spray nozzle that creates a spray cone 56 of small droplets of the liquid material that is substantially uniformly delivered to the heater assembly 24.

The heater assembly 24 is electrically connected via wiring 58 with power source 14 and is controlled by control unit 16. Control unit 16 is in communication via wiring 60 with electrical switch 62 that is coupled to button 48. Thus, simultaneously with activating the manually operated pump via button 48, an electrical signal is created via electrical switch 62, whereupon control unit 16 activates heater assembly 24 for volatilization of the delivered liquid aerosol-forming substrate.

While pressing button 48 a puff or draw at the mouthpiece 28 is taken, creating an airstream between air inlet 26 and mouthpiece 28. The volatilized liquid aerosol-forming substrate mixes with the airstream creating an aerosol.

Figure 3:
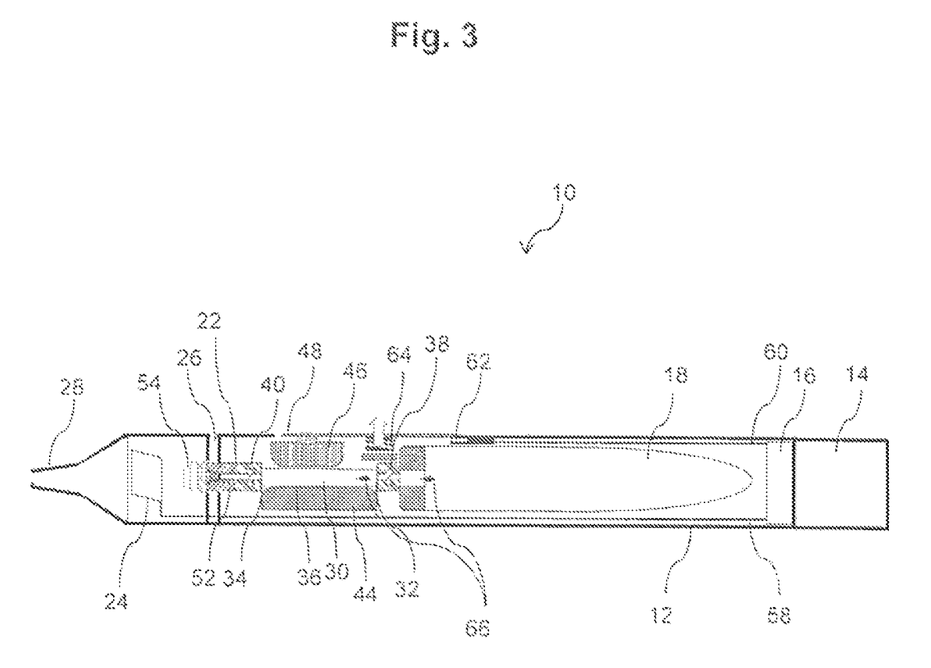
FIG. 3 is a cross-sectional view of the aersol-generating system of FIG. 2 after manual activation of the volume modifier according to at least one example embodiment.

When button 48 is released, as depicted in FIG. 3, the moveable element 46 is returned to its original position by resilient spring member 64. Hollow tube 30 resumes its original size creating an underpressure in the pumping volume 36. In order to compensate the underpressure, fresh liquid aerosol-forming substrate is pumped from the liquid storage portion 18 via inlet valve 38 into the pumping volume 36. This is indicated by arrow 66 in FIG. 3. In this example embodiment, the liquid storage portion 18 comprises a collapsing bag. The volume of the collapsing bag reduces as the liquid aerosol-forming substrate is pumped out of the liquid storage portion 18.

The example embodiment described above relies on a flexible wall to allow the internal volume of the hollow member to be modified. However, other ways of modifying the volume of a hollow member are possible.

Figure 4:
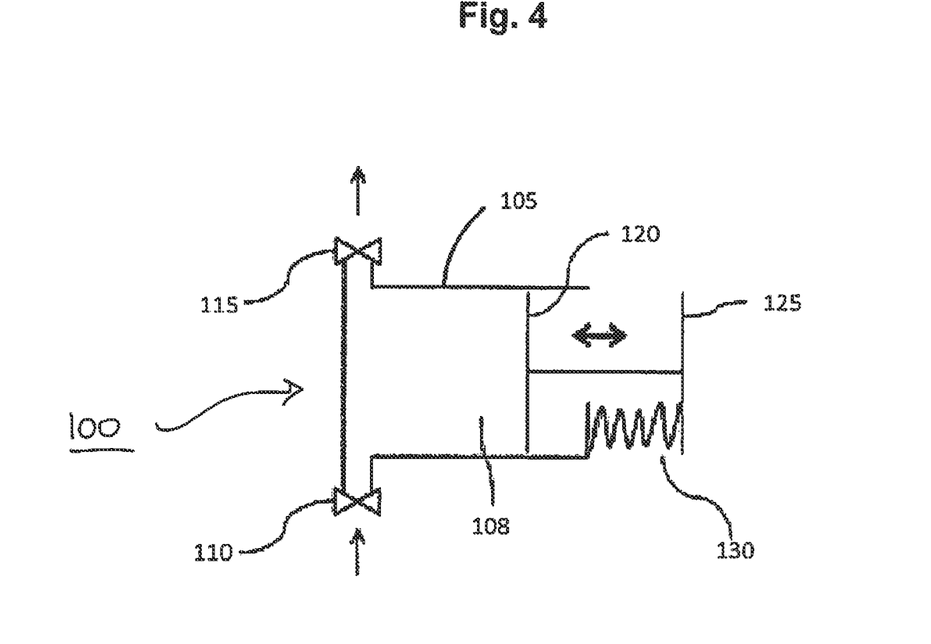
FIG. 4 is a schematic illustration of an alternative mechanism for modifying the internal volume of the hollow member according to at least one example embodiment.

FIG. 4 is a schematic illustration of an alternative mechanism for modifying the internal volume of a hollow member in a manually operated pump.

In at least one example embodiment, as shown in FIG. 4, the hollow member 100 comprises a rigid wall 105 containing a volume of liquid. The hollow member 100 is connected to a liquid storage portion through an inlet valve 110 and to a heater assembly through an outlet valve 115, in the manner described with reference to FIGS. 1 to 3. A plunger 120 is movable within the hollow member 100 and maintains a liquid tight seal with the rigid wall 105 as it moves. The internal volume 108 of the hollow member is defined between the rigid wall 105, the inlet valve 110, the outlet valve 115 and the plunger 120. Movement of the plunger within the hollow member changes the internal volume. The plunger is fixed to a button 125 that can be pressed to move the plunger to move the plunger to reduce the internal volume of the hollow member. A return spring 130 is provided between the button and the rigid wall 105 to return the plunger to an initial position when the button is released. When the button is pressed, liquid in the hollow member is forced out through the outlet valve 115 and when the button is released, the plunger returns to its initial position and liquid is drawn into the hollow member through the inlet valve 110.

The exemplary embodiments described above illustrate but are not limiting. In view of the above discussed exemplary embodiments, other embodiments consistent with the above exemplary embodiment will now be apparent to one of ordinary skill in the art.

We claim:

1. An aerosol generating system comprising:
   a heater assembly,
   a liquid storage portion configured to contain a liquid material;
   a dispensing assembly configured to dispense the liquid material to the heater assembly; and
   a pump including,
      a flexible, hollow tube having an inlet and an outlet, the inlet connected to the liquid storage portion, and the outlet in fluid communication with the dispensing assembly, and
      a volume modifier including,
         a fixed element in contact with the flexible, hollow tube, and
         a moveable element connected to a button in a housing of the aerosol generating system, the flexible, hollow tube between the fixed element and the moveable element, such that when the button is pressed, the button presses against the moveable element so as to press the moveable element against the flexible, hollow tube in a direction towards the fixed element.

2. The aerosol generating system of claim 1, wherein the inlet and the outlet each include a one-way valve.

3. The aerosol generating system of claim 2, wherein the one-way valve at the inlet is configured to allow the liquid material to flow from the liquid storage portion into the flexible, hollow tube.

4. The aerosol generating system of claim 2, wherein the one-way valve at the outlet is configured to allow the liquid material to flow from the flexible, hollow tube to the dispensing assembly.

5. The aerosol generating system of claim 1, wherein the pump is manually operated.

6. The aerosol generating system of claim 1, wherein the volume modifier further comprises:
a resilient element configured to assist in returning the moveable element to a resting position.

7. The aerosol generating system of claim 1, wherein the dispensing assembly comprises:
a nozzle configured to spray the liquid material onto the heater assembly.

8. The aerosol generating system of claim 1, wherein upon activation of the pump, an amount of the liquid material is delivered onto the heater assembly via the dispensing assembly.

9. The aerosol generating system of claim 1, wherein the heater assembly comprises an electrical resistive heating element, a metallic mesh, a metallic thin film coating applied on a non-conductive heat resistant substrate, or any combination thereof.

10. The aerosol generating system of claim 1, wherein the moveable element is coupled to an electronic switch, and the electronic switch is configured to create an electrical signal in response to the moveable element being operated.

11. The aerosol generating system of claim 10, wherein the electronic switch is a kinetic electronic switch, and signals from actuation of the kinetic electronic switch are transmitted
to a control unit via a wireless communication channel.

12. A method of delivering a liquid material in an aerosol generating system comprising
providing an aerosol generating system including,
a heater assembly,
a liquid storage portion configured to contain a liquid material;
a dispensing assembly configured to dispense the liquid material to the heater assembly; and
a pump including,
a flexible, hollow tube having an inlet and an outlet, the inlet connected to the liquid storage portion, and the outlet in fluid communication with the dispensing assembly, and
a volume modifier including,
a fixed element in contact with the flexible, hollow tube, and
a moveable element connected to a button in a housing of the aerosol generating system, the flexible, hollow tube between the fixed element and the moveable element, such that when the button is pressed, the button presses against the moveable element so as to press the moveable element against the flexible, hollow tube in a direction towards the fixed element; and
operating the pump so as to pump the liquid material from the liquid storage portion onto the heater assembly via the dispensing assembly.

13. The method of claim 12, wherein the inlet and the outlet each include a one-way valve.

14. The method of claim 13, wherein the one-way valve at the inlet allows the liquid material to flow from the liquid storage portion into the flexible, hollow tube.

15. The method of claim 13, wherein the one-way valve at the outlet allows the liquid material to flow from the flexible, hollow tube to the dispensing assembly.

16. The method of claim 12, further comprising:
generating an electronic signal, using an electronic switch operably connected to the moveable element, in response to the moveable element being activated.

17. The method according to claim 16, wherein the electronic switch is a kinetic manually powered electronic switch.

18. The method according to claim 17, further comprising:
transmitting the electronic signal to a control unit via a wireless communication channel.

\* \* \* \* \*